United States Patent [19]
Herkes et al.

[11] Patent Number: 5,877,314
[45] Date of Patent: Mar. 2, 1999

[54] PROCESS TO CONTINUOUSLY PREPARE AN AQUEOUS MIXTURE OF EPISILON CAPROLACTUM AND EPISILON CAPROLACTUM PRECURSORS

[75] Inventors: Frank E. Herkes, Wilmington, Del.; Robert Pestman, Eindhoven; Jeroen A.F. Boogers, Maastricht, both of Netherlands

[73] Assignees: DSM N.V., Heerlen, Netherlands; E.I. DuPont de Nemours and Company, Wilmington, Del.

[21] Appl. No.: 800,324

[22] Filed: Feb. 14, 1997

[51] Int. Cl.$^6$ ....................... C07D 201/02; C07D 201/16
[52] U.S. Cl. ............................. 540/538; 540/540
[58] Field of Search ...................... 540/538, 540

[56] References Cited

U.S. PATENT DOCUMENTS

| | | | |
|---|---|---|---|
| 4,730,040 | 3/1988 | Vagt et al. | 540/538 |
| 4,950,429 | 8/1990 | Vagt et al. | 260/404 |
| 4,963,672 | 10/1990 | Merger et al. | 540/538 |
| 5,068,398 | 11/1991 | Merger et al. | 560/156 |
| 5,700,934 | 12/1997 | Wolters et al. | 540/538 |
| 5,717,089 | 2/1998 | Wolters et al. | 540/538 |

FOREIGN PATENT DOCUMENTS

| | | |
|---|---|---|
| 729 944 | 2/1996 | European Pat. Off. . |
| 729 943 | 9/1996 | European Pat. Off. . |

Primary Examiner—Mukund J. Shah
Assistant Examiner—Bruck Kifle
Attorney, Agent, or Firm—Pillsbury Madison & Sutro LLP

[57] ABSTRACT

This continuous process for preparing an aqueous mixture of ∈-caprolactam and 6-aminocaproic acid and/or 6-aminocaproamide by involves, as the reductive amination step, continuously contacting 5-formylvaleric acid or an alkyl 5-formylvalerate in water as solvent with hydrogen and an excess of ammonia in the presence of a ruthenium on carrier, as a catalyst, wherein the carrier is at least one of titanium oxide or zirconium oxide. The aqueous mixture can be used to prepare ∈-caprolactam.

14 Claims, No Drawings

PROCESS TO CONTINUOUSLY PREPARE AN AQUEOUS MIXTURE OF EPISILON CAPROLACTUM AND EPISILON CAPROLACTUM PRECURSORS

FIELD OF THE INVENTION

The present invention relates to a process to continuously prepare an aqueous mixture of ∈-caprolactam and 6-aminocaproic acid and/or 6-aminocaproamide by continuously contacting 5-formylvaleric acid or an alkyl 5-formylvalerate with hydrogen and an excess of ammonia in the presence of a ruthenium on carrier catalyst.

DESCRIPTION OF THE PRIOR ART

A process for preparing ∈-caprolactam is described in U.S. Pat. No. 4,730,040. In this process, methyl 5-formylvalerate is first hydrolyzed (step x) in the presence of water and an acidic agent to yield 5-formylvaleric acid. In this process, the 5-formylvaleric acid is reductively aminated in water through contact with ammonia and hydrogen using a ruthenium/zirconium on alumina catalyst or a Raney Nickel catalyst to obtain a 6-aminocaproic acid containing reaction mixture. After separation of ammonia, the reaction mixture obtained from the reductive amination is heated to 300° C. to form ∈-caprolactam by cyclization of the 6-aminocaproic acid. A disadvantage of the process according to U.S. Pat. No. 4,730,040 is the poor yields obtined from the reductive amination which present it from being a commercially attractive process. According to the experimental results, the best yield of the hydrolysis step is only about 78%, the best yield of the reductive amination step is only about 77% and the best yield of the final step is only about 95%. Hence, the overall yield is at most 57%.

Another disadvantage is that when the reductive amination is performed for a prolonged period of time, a decrease in particle size of the Raney Nickel and alumina catalyst particles has been found to occur. This is not desired because these small particles may disturb any filtration operation or lead to catalyst losses due to entrainment of the catalyst in the product stream.

A still further disadvantage is that after some hours of continuous operation the activity of the catalyst can decrease.

Therefore, there has been a need for facile process for producing ∈-caprolactam in a high yield.

SUMMARY AND OBJECTS OF THE INVENTION

An object of the present process is to reproducibly obtain a higher yield to ∈-caprolactam and ∈-caprolactam precursors (6-aminocaproic acid and 6-aminocaproamide) in the reductive amination without suffering the above described problems, including the decrease of the catalyst particle size or loss of catalyst activity.

This and other objects are achieved in the present continuous process by preparing an aqueous mixture of ∈-caprolactam and 6-aminocaproic acid and/or 6-aminocaproamide by continuously contacting 5-formylvaleric acid or an alkyl 5-formylvalerate in water (as solvent) with hydrogen and an excess of ammonia in the presence of a ruthenium on a carrier as a catalyst, wherein the carrier is titanium oxide or zirconium oxide. The aqueous mixture from the one-step reductive amination can be used to prepare ∈-caprolactam.

It has been found that when the process according to the invention is performed a high yield to ∈-caprolactam and ∈-caprolactam precursors can be achieved in the reductive amination, and the catalyst retains its particle size and activity over a prolonged period of time. Another advantage is that when starting from an alkyl 5-formylvalerate a separate hydrolysis step in order to prepare 5-formylvaleric acid, such as described in U.S. Pat. No. 4,730,040, is not needed. This is very advantageous because the separate hydrolysis of the alkyl 5formylvalerate as described in U.S. Pat. No. 4,730,040 showed a low yield (78%) to 5-formylvaleric acid. It has been found that the alkyl 5formylvalerate can be directly used in the present process, resulting in a high yield to ∈-caprolactam while avoiding the low-yield-hydrolysis step described in U.S. Pat. No. 4,730, 040.

According to EP-A-729943 and EP-A-729944 ∈-caprolactam can be prepared by first contacting methyl 5-formylvalerate with ammonia and subsequently reacting the intermediate compounds thus formed, probably imine-caproic acid derivatives, with hydrogen in the presence of ammonia and, for example, a ruthenium on alumina catalyst or Raney Nickel. These patent applications mention zirconium oxide and titanium oxide as possible carrier materials for nickel, cobalt or ruthenium catalysts. However, only ruthenium on alumina carriers are used in the examples of EP-A-729943 and EP-A-729944. By performing the reductive amination in two steps the yield to ∈-caprolactam and ∈-caprolactam precursors is increased according to the patent publications. However when using the exemplified ruthenium on alumina catalyst the earlier mentioned problem of particle size reduction also takes place. It was therefore not expected that by using a ruthenium on zirconium or titanium oxide carrier in a one-step reductive amination that a high yield to ∈-caprolactam precursors could be achieved while at the same time avoiding loss of catalyst activity and reduction of catalyst particle size.

DETAILED DESCRIPTION OF THE INVENTION

The alkyl 5-formylvalerate compound is preferably a $C_1$–$C_6$ alkyl 5-formylvalerate compound. Examples of suitable alkyl groups are methyl, ethyl, propyl, iso-propyl, tert-butyl, n-butyl, iso-butyl, cyclohexyl. More preferably methyl and ethyl groups are used because methyl- and ethyl-5-formylvalerate are readily obtainable such as, for example, by the processes described in U.S. Pat. No. 5,527, 950, WO-A-9404482 and WO-A-9506025, the complete disclosures of which are incorporated by reference. A method for preparing 5-formylvaleric acid starting from a pentenoic acid is, for example, described in WO-A-9518783, the complete disclosure of which is incorporated herein by reference. Preferably the starting compound is an alkyl 5-formylvalerate because these compounds are more readily available than 5-formylvaleric acid. Unless otherwise stated, reference herein to the formyl-starting compound means alkyl 5-formylvalerate, 5-formylvaleric acid, or both.

The reductive amination is performed by contacting the formyl-starting compound in water with hydrogen and a molar excess of ammonia in the presence of a ruthenium on titanium oxide or ruthenium on zirconium oxide, as the catalyst.

A relatively small but catalytically effective amount of the catalyst is used in the present process. The amount of ruthenium (as metal) in the catalyst is generally between 0.1 and 10 wt %. The mean particle size ($d_{50}$) is preferably between 10 and 100 µm, when the catalyst is present as a slurry in the reaction mixture or between 0.001 and 0.05 m, when the catalyst is present in a fixed bed. The BET surface area can be between 1 and 100 $m^2/g$. The BET surface area is preferably between 30 and 100 $m^2/g$. Preferably anatase is used to reach such a high BET surface area titanium oxide. The high BET surface area is advantageous because higher catalyst activity can be obtained.

Titanium oxide is preferably used as the carrier because of its high chemical and mechanical stability and because the selectivity to the preferred (intermediate) compounds is found to be relatively high when this support is used.

The water content in the reaction mixture as described above is at least 10 wt % and more preferably between about 15 and about 60 wt % and most preferably between about 20 and about 50 wt %.

The molar ratio of ammonia and formyl-starting compound in the reductive amination step is preferably between about 3:1 and about 30:1, and more preferably is between about 5:1 and about 15:1.

The temperature is preferably between about 40° C. and about 200° C., and more preferably between about 80° C. and about 160° C.

The process is preferably conducted under pressure. In general, the pressure is equal or greater than the resulting equilibrium pressure of the liquid reaction mixture employed. The pressure is preferably between 0.5 and 10 MPa.

The molar amount of hydrogen is at least equal to the molar quantity of formyl-starting compound. The molar ratio of hydrogen to the formyl-starting compound is preferably between about 1.00 to about 100.

If the starting compound is an alkyl 5-formylvalerate it is preferred that some alcohol, corresponding to this alkyl group is present in the reaction mixture. The concentration of the corresponding alcohol can be between 1 and 15 wt. %, although the alcohol concentration is preferably between 5 and 15 wt % in order to improve the solubility of the alkyl 5-formylvalerate when the concentration of the latter compound is relatively high (>15 wt. %).

The reaction mixture obtained in the process according to the invention comprises ∈-caprolactam and 6-aminocaproic acid, ammonia, water and some dissolved hydrogen. If the starting compound is an alkyl 5-formylvalerate, 6-aminocaproamide, a small amount of alkyl 6-aminocaproate and the corresponding alcohol to the alkyl will be present in the reaction mixture. Some oligomers of 6-aminocaproic acid and/or of 6-aminocaproamide may also be formed when the present process is conducted at relatively higher substrate concentrations. These oligomers, e.g., 6-aminocaproic acid, 6-aminocaproamide and the alkyl 6-aminocaproate, are all precursors to ∈-caprolactam.

The present invention can be performed continuously in a fixed bed reactor in which the heterogeneous hydrogenation catalyst is present. An advantage of this reactor is that the reactants are easily separated from the hydrogenation catalyst. Another manner of performing the reductive amination is by way of one or more continuously operated well mixed contactors in series in which the hydrogenation catalyst is present as a slurry (slurry reactor). This manner of operation has the advantage that the heat of the reaction can be easily controlled by, for example, a cooled feed or by way of internally placed cooling devices. Examples of specific and suitable slurry reactors are one or multiple staged bubble columns or a gas lift-loop reactor or a continuously stirred tank reactor (CSTR). The slurry-hydrogenation catalyst can be separated from the reaction mixture by for example using hydrocyclones and/or by filtration, for example by cake- or cross-flow filtration.

The catalyst concentration can be suitably selected across a wide concentration range. In a fixed bed reactor the amount of catalyst per reactor volume will be high, while in a slurry-reactor this concentration will, in general be lower. In a continuously operated slurry reactor the weight fraction of catalyst (including the carrier) is typically between about 0.1 and about 30 weight % relative to the total reactor content. of the reactor.

Ammonia, hydrogen, the heterogeneous hydrogenation catalyst and the alcohol (if present) are preferably separated from the reaction mixture obtained in the reductive amination prior to the cyclization step to ∈-caprolactam. Hydrogen and part of the ammonia can advantageously be separated from this reaction mixture by reducing the pressure and performing a gas/liquid separation. An example of such an operation is a flash operation performed at between ambient about pressure and about 0.5 MPa. Advantageously, the hydrogen and ammonia can be recycled to the reductive amination step.

In a step subsequent to the reductive amination, the alcohol (if present) can be separated. It has been found that it is advantageous to cyclize the ∈-caprolactam precursors to ∈-caprolactam in the presence of 0 wt. % to 1 wt %, and more preferably from 0 wt. % to less than 0.1 wt % of alcohol. Thus, when the mixture, resulting from the reductive amination contains alcohol, it is advantageous to separate this alcohol compound. It has been discovered that the presence of alcohol during the cyclization promotes the formation of the corresponding N-alkyl caprolactam, an undesired by-product. The presence of small quantities of these N-alkylated by-products, for example N-methyl ∈-caprolactam, in the final ∈-caprolactam renders the ∈-caprolactam less suitable for use as starting material for preparing nylon-6 fibers. These N-alkylated products (especially N-methyl- and N-ethyl caprolactam) are difficult to separate from the final ∈-caprolactam. Consequently, it is highly desired to avoid or minimize their formation in the process according to the invention.

Separating the alcohol from the mixture obtained in from the reductive amination according to the invention can be performed by suitable methods known to those skilled in the art for example distillation, or stripping.

The ∈-caprolactam precursors present in the aqueous mixture are preferably further reacted to ∈-caprolactam. This reaction step (hereinafter referred to as the cyclization step) can be performed in the gas phase as described in for example U.S. Pat. No. 4,599,199 or in U.S. Pat. application No. 3,658,810, the complete disclosures of which are incorporated herein by reference, by contacting a mixture, preferably concentrated, as obtained in the reductive amination with overheated steam having a temperature of about 150° C. and about 400° C. at about atmospheric pressure. The gas phase processes are advantageous because ∈-caprolactam is obtained in a gaseous steam phase in which no oligomers are present. Separation of ∈-caprolactam and oligomers can thus be avoided.

The cyclization is preferably performed in the liquid phase at super atmospheric pressures such as, for example, described in the aforementioned U.S. Pat. No. 4,730,040 and EP-A-729944. High yields of ∈-caprolactam of high quality can be obtained with a liquid phase cyclization process. More preferably a liquid phase cyclization is performed as discussed below.

The concentration of ammonia in the cyclization is preferably above about 0 wt. % and below about 5 wt. % and more preferably below about 3 wt. % and most preferably below about 1 wt. %. High concentrations of ammonia have a negative effect on the yield to ∈-caprolactam per pass in a continuous process.

The concentration of ∈-caprolactam and ∈-caprolactam precursors in the cyclization is preferably between about 5 and about 50 wt. % and more preferably between about 10 and about 35 wt. %.

The elevated temperature of the cyclization is preferably between about 200° C. and about 350° C., and more preferably the temperature is higher than about 290° C. because a higher yield to ∈-caprolactam per pass is possible.

The pressure is preferably between about 5.0 and about 20 MPa. Normally this pressure will be greater than or equal to the resulting pressure of the liquid reaction mixture and the temperature employed.

The cyclization can be performed continuously in process equipment resulting in high and low rates of backmixing, such as described in EP-A-729944.

The ∈-caprolactam can be separated from the reaction mixture obtained in the cyclization by for example crystallization, extraction or by distillation. The ∈-caprolactam is preferably separated by extraction. Suitable extraction solvents include $C_1$–$C_{10}$ chlorinated hydrocarbons and $C_6$–$C_{25}$ alkyl phenols, such as chloroform, dichloromethane, 1,1,1-trichloromethane, docecyl phenol, octyl phenol, and nonyl phenol.

Preferred extraction solvents are (cyclic)aliphatic organic compounds having one or more hydroxy groups, e.g., (poly) alcohols, which are liquid under the extraction conditions and substantially immiscible with water. These (poly) alcohols preferably have 5 to 12 carbon atoms. These extraction agents are preferred because they have a better extraction efficiency than the chloronated organic compounds. Preferably one or two and more preferably only one hydroxy group is present. Suitable compounds having two hydroxy groups include, for instance, hexanediol, nonanediol, neopentylglycol, methyl-methylpropanediol, ethyl-methylpropanediol or butyl-methylpropanediol or a mixture of any of these. Suitable compounds having one hydroxy group include, for instance, cyclohexanol, 4-methyl-2-pentanol, 2-ethyl-1-hexanol, 2-propyl-1-heptanol, n-octanol, iso-nonylalcohol, n-decylalcohol and mixtures of linear and branched $C_8$-alcohols, mixtures of linear and branched $C_9$-alcohols and mixtures of linear and branched $C_{10}$-alcohols. Mixtures of the above described (poly)- and mono-alcohols are also suitable extraction solvents.

Prior to this extraction step it is preferred to separate part or all of the ammonia present in the aqueous mixture obtained in the reductive amination in order to prevent a build up of ammonia in the process.

Extraction of ∈-caprolactam from the effluent of the cyclization is especially advantageous over distillation when oligomers are also present in the aqueous mixture containing the ∈-caprolactam. When using distillation, a high concentration of oligomers is usually obtained in the residue of the distillation(s). The oligomers can solidify, and therefore a high concentration can foul, for instance, pipes and other process equipment. This disadvantage does not occur when extraction is used as a method for isolating ∈-caprolactam.

Another advantage of extraction over distillation is that the amine compounds which can be present in the effluent of the cyclization are not exposed to the high reboiler temperatures of the distillation. Under these high reboiler temperature conditions by-products and (more) oligomers tend to be formed. Exposure of the ∈-caprolactam precursors to the high temperatures of the reboilers can be avoided by using extraction as the method for isolating ∈-caprolactams. The ∈-caprolactam can be purified by methods known for purifying ∈-caprolactam obtained by Beckmann rearrangement. An exemplary method of purifying ∈-caprolactam is described in U.S. Pat. No. 5,496,941, the complete disclosure of which is incorporated by reference.

The complete disclosures of all patents and literature cited in this specification are hereby incorporated be reference.

The following non-limiting examples further describe the invention.

EXAMPLES

Example 1

40 grams of 5 wt % ruthenium on titanium oxide were introduced in a 1 liter Hastelloy-C reactor. After the addition of water, the catalyst was pre-reduced at 140° C. during 12 hours. Subsequently, an aqueous stream consisting of 25 wt. % methyl-5-formylvalerate, 35 wt. % ammonia and 7 wt. % methanol in water, was fed continuously to the reactor at a rate of 775 grams/hour. The reactor was kept at a constant pressure of 4.0 MPa by a hydrogen stream of 10 grams per hour. The reaction was performed at 120° C.

During 96 hours the effluent which continuously left the reactor was analyzed at regular intervals. A constant yield of desired products, i.e. ∈-caprolactam and caprolactam precursors, of 97% was obtained.

Comparative Experiment A

Example 1 was repeated but with 212 grams of 5 wt. % ruthenium on alumina ($d_{50}$: 74 μm), 30 wt. % ammonia in the feed and a total pressure of 3.0 MPa.

The yield of desired products was 98%. However, after 200 hours the $d_{50}$ was 1 μm, making this catalyst not suitable for use in a large scale process.

Comparative Experiment B 50 grams of Raney-Nickel were introduced in a 1 liter Hastelloy-C reactor. An aqueous stream consisting of 5 wt. % methyl-5formylvalerate and 20 wt. % ammonia in water, was fed continuously to the reactor at a rate of 875 grams/hour. The reactor was kept at a constant pressure of 1.5 MPa by a hydrogen stream of 10 grams per hour. The reaction was performed at 100° C.

The yield of desired products was 96% during the first 6 hours. However, within 18 hours the yield decreased to 48% and only 21 grams of catalyst was left over in the reactor. This catalyst loss makes this catalyst not suitable for a large scale process.

Example 2

1 gram of 3.5 wt. % ruthenium on titanium oxide (BET surface area 3.4 $m^2$/g) was introduced in a 100 ml autoclave. The catalyst was reduced in 57 grams of water at 175° C. at 5.0 MPa hydrogen during 1 hour. After addition of 23.1 grams ammonia, the temperature was brought to 100° C. and the pressure to 5.0 MPa, the pressure being raised with the temperature and maintained at that level for 3 hours. Subsequently 2.8 grams methyl-5-formylvalerate and 1.8 grams methanol were added. The calculated first order reaction coefficient was $84 \times 10^{-4}$ per second.

Example 3

Example 2 was repeated with 1 gram of 4.2 wt. % ruthenium on titanium oxide (BET surface area 48 $m^2$/g). The calculated first order reaction coefficient was $297 \times 10^{-4}$ per second.

Comparison of Example 2 and 3 illustrates that a 3.5x higher catalyst activity is obtained when using higher BET surface area titanium oxide carriers.

What we claim is:

1. A continuous process for preparing aqueous mixture of ∈caprolactam and 6-aminocaproic acid and/or 6-aminocaproamide which comprises the step of continuously reductively aminating at least one of 5-formylvaleric acid or an alkyl 5-formylvalerate, in water, with hydrogen and an excess of ammonia in the presence of ruthenium on carrier as a catalyst, wherein the carrier is at least one of titanium oxide or zirconium oxide.

2. A process according to claim 1, wherein the amount of ruthenium in the catalyst is between 0.1 and 10 wt %.

3. A process according to claim 1 or 2, wherein the particle size of the catalyst is between 10 and 100 $\mu$m and the step is performed in a slurry phase reactor.

4. A process according to of claim 1 or 2, wherein the particle size of the catalyst is between 0.001 and 0.05 m and the step is performed in a fixed bed reactor.

5. A process according to claim 1 or 2, wherein the catalyst has a BET surface area of between 30 and 100 $m^2/g$.

6. A process according to claim 1 or 2, wherein the step is performed in a fixed bed reactor and the catalyst has a particle size between 10 $\mu$m and 100 $\mu$m.

7. A process according to claim 1 or 2, wherein the carrier is titanium oxide.

8. A process according to claim 5, wherein the carrier is titanium oxide.

9. A process according to claim 1 or 2, wherein said alkyl 5formylvalerate is $C_1$–$C_6$ alkyl 5-formylvalerate.

10. A process according to claim 9, wherein the catalyst has a BET surface area of between 30 and 100 $m^2/grams$, and the carrier is titanium oxide.

11. A process for preparing ∈-caprolactam using the aqueous mixture obtained according to claim 1 or 2.

12. A process for preparing ∈-caprolactam comprising the steps of heating the mixture obtained in the process according claim 1 or 2 to a temperature effective for cyclizing ∈-caprolactam precursors in said mixture in the liquid phase; and extracting the thus produced ∈-caprolactam from the mixture.

13. A process according to claim 12, wherein said extraction step is performed using an alcohol having 5–12 carbon atoms as an extraction agent.

14. A process according to claim 12, wherein said heating is at a temperature of about 290° C. to about 350° C.

* * * * *